US008927685B1

(12) United States Patent
Davis

(10) Patent No.: US 8,927,685 B1
(45) Date of Patent: *Jan. 6, 2015

(54) THERMOSET AND THERMOPLASTIC COMPOSITIONS DERIVED FROM THE ESSENTIAL OILS OF HERBS

(71) Applicant: The United States of America as Represented by the Secretary of the Navy, Washington, DC (US)

(72) Inventor: Matthew C. Davis, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 16 days.

This patent is subject to a terminal disclaimer.

(21) Appl. No.: 14/030,179

(22) Filed: Sep. 18, 2013

Related U.S. Application Data

(63) Continuation-in-part of application No. 13/875,459, filed on May 2, 2013, and a continuation-in-part of application No. 13/874,743, filed on May 1, 2013.

(60) Provisional application No. 61/703,691, filed on Sep. 20, 2012, provisional application No. 61/647,686, filed on May 12, 2012, provisional application No. 61/647,678, filed on May 16, 2012.

(51) Int. Cl.
| | | |
|---|---|---|
| *C08G 75/02* | (2006.01) | |
| *C08G 65/38* | (2006.01) | |
| *C07C 263/00* | (2006.01) | |
| *C07C 265/14* | (2006.01) | |
| *C08C 2/06* | (2006.01) | |

(52) U.S. Cl.
CPC .............. *C08G 65/38* (2013.01); *C07C 263/00* (2013.01); *C07C 265/14* (2013.01)
USPC ........................... 528/499; 528/210; 528/315

(58) Field of Classification Search
USPC ........................................ 528/210, 499, 315
See application file for complete search history.

(56) References Cited

U.S. PATENT DOCUMENTS

| | | | |
|---|---|---|---|
| 3,922,368 | A | 11/1975 | Klaul et al. |
| 5,260,398 | A | 11/1993 | Liao et al. |
| 5,406,003 | A | 4/1995 | Wang et al. |
| 7,439,353 | B2 | 10/2008 | Matsuo et al. |
| 7,825,169 | B2 | 11/2010 | Wada et al. |
| 2002/0058778 | A1 | 5/2002 | Konarski et al. |
| 2012/0165429 | A1 | 6/2012 | Boulevin et al. |

FOREIGN PATENT DOCUMENTS

| | | |
|---|---|---|
| EP | 2167478 | 3/2010 |
| JP | 01290642 | 11/1989 |
| WO | WO 0055123 | 9/2000 |

OTHER PUBLICATIONS

U.S. Appl. No. 13/874,743, filed May 1, 2013 Inventor(s) Davis, Matthew et al.*
High Tg thermosetting resins from resveratrol Poly. Chem.(2013), 4(13), 3859-3865 CODEN: PCOHC2; ISSN: 1759-9962; Eng.Rec. Apr. 4, 2013, Acc.d 25th April 20.

* cited by examiner

*Primary Examiner* — Terressa Boykin
(74) *Attorney, Agent, or Firm* — Charlene A. Haley

(57) ABSTRACT

A renewable chemical feedstock derived from the essential oils from herbs and other plants. In embodiments, trans-anethole are transformed into thermoset and thermoplastic compositions.

25 Claims, No Drawings

THERMOSET AND THERMOPLASTIC COMPOSITIONS DERIVED FROM THE ESSENTIAL OILS OF HERBS

CROSS-REFERENCE TO RELATED APPLICATIONS

This is a non-provisional patent application, claiming the benefit of, parent application Ser. No. 61/703,691 filed on Sep. 20, 2012 and is a continuation-in-part patent application of Ser. No. 13/875,459 filed on May 2, 2013 which is a non-provisional patent application of provisional patent application Ser. No. 61/647,686 filed on May 16, 2012 and in a continuation-in part of patent application Ser. No. 13/874,743 filed on May 1, 2012 which is a non-provisional of provisional patent application Ser. No. 61/647,678 filed on May 16, 2012, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to renewable feedstocks, and more particularly, to renewable chemical feedstocks derived from the essential oils from herbs and other plants.

DESCRIPTION OF EMBODIMENTS OF INVENTION

Thermosetting resins are uncured and at room temperature they are in a liquid state. Thermosetting resins can exhibit properties including: great adhesion, great finishing as in polishing and painting, resistance to solvents and corrosives, resistance to heat and high temperature, fatigue strength, and tailored elasticity. In a thermoset resin, the raw uncured resin molecules are crossed linked through a catalytic chemical reaction. Through this chemical reaction, most often exothermic, the resin creates extremely strong bonds to one another, and the resin changes state from a liquid to a solid. A thermosetting resin, once catalyzed, it cannot be reversed or reformed. Meaning, once a thermoset composite is formed, it cannot be remolded or reshaped. Because of this, the recycling of thermoset composites is extremely difficult. The thermoset resin itself is not recyclable, however, there are a few new companies who have successfully removed the resin through pyrolization and are able to reclaim the reinforcing fiber. Thermoplastic resins are most commonly=reinforced, meaning, the resin is formed into shapes and have no reinforcement providing strength. Many thermoplastic products use short discontinuous fibers as a reinforcement. There are two major advantages of thermoplastic composites. The first is that many thermoplastic resins have an increased impact resistance to comparable the set composites. In some instances, the difference is as high as 10 times the impact resistance. An advantage of thermoplastic composites is the ability reform and thermoplastic composites, at room temperature, are in a solid state. When heat and pressure impregnate a reinforcing fiber, a physical change occurs; not a chemical reaction as with a thermoset. This allows thermoplastic composites to be reformed and reshaped. (Thermoplastic vs Thermoset Resins from about.com)

In embodiments of the invention, thermosets can be conveniently prepared from the extracts from the essential oils mainly from herbs and other plants. The prepared products can be polymerized or cured into materials with high heat resistance. Decreased reliance on petrochemicals is realized. Applications include aerospace uses requiring high strength-to-weight ratios because the novel materials are lightweight and thermally resistant.

The Navy and Department of Defense (DoD) are heavily dependent on petroleum for sources of mission-critical composite materials. Embodiments of the invention address this issue by employing readily essential oils from plants to make new composite materials. The composite materials may find uses in aerospace applications. The essential oil products from plants represent a renewable resource for resins and plastics.

There are many plants, especially herbs, which provide essential oils when extracted. In particular tarragon (*Artemisia dracunculus*) and star anise (*Illicium verum*) yield essential oils that are almost exclusively the isomers of 4-methoxyphenylpropene (estragole and anethole). These products transform by the reaction known as olefin metathesis (Chemical Schematic 1) to give new products that are dimeric in structure having two equivalents of protected phenolic groups in the molecule. The catalyst to carry out this transformation is commercially available to those skilled in the art. The formed point of unsaturation can be reduced or not and then the methyl ethers can be deprotected to yield the new diphenolic products. The diphenolic products from natural and renewable sources can then be inserted into the many known polymerization reactions (Chemical Schematic 2) to those skilled in the art including, but not limited to, polyesters, polycarbonates, polycyanurates, polyurethanes, polyetherimides, polyetheretherketones, and polysulfones.

Chemical Schematic 1 is an example derivation of essential oils from tarragon and star anise to prepare diphenol(s) building blocks.

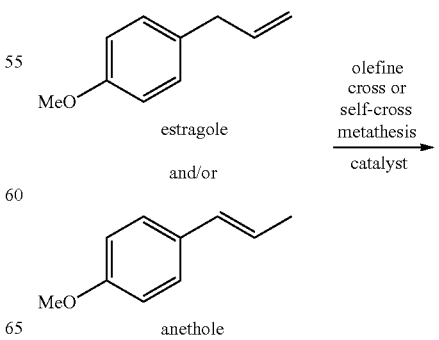

-continued

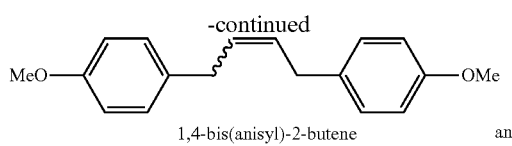

1,4-bis(anisyl)-2-butene    and/or

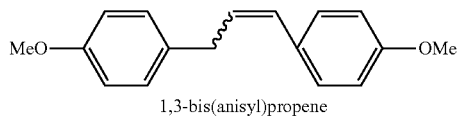

1,3-bis(anisyl)propene    and/or

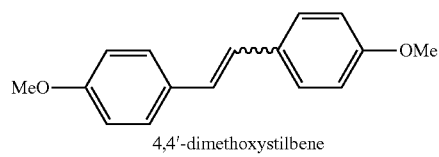

4,4'-dimethoxystilbene

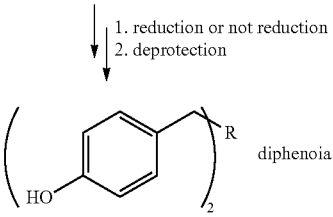

diphenoia

There are also some embodiments for copolymerization using sequential or mixed additions to the phenolic compounds.

Scheme 3: Dimerization of trans-anethole into linear or tricyclic diphenols.

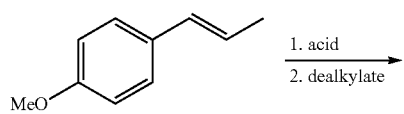

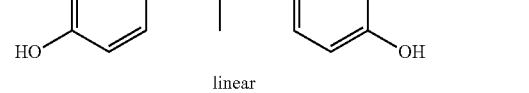

AND/OR linear

Chemical Schematic 2 is an example of polymerization possibilities of plant derived monomers.

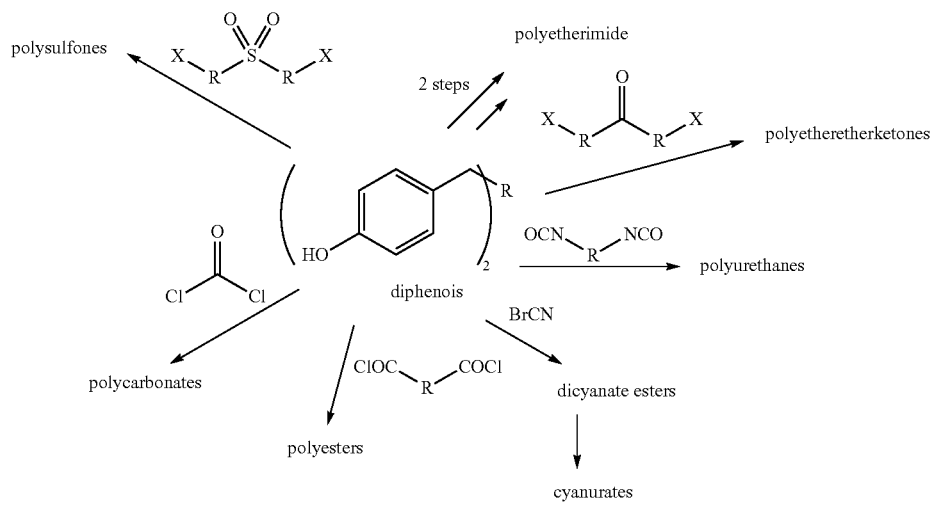

In addition, trans-anethole can be dimerized into two different dimers, one di-cyclic and the other tricyclic, by a variety of different acid catalyst (Scheme 3). The resulting diphenols of these dimers possess significantly different properties which will also affect the resulting polymers made thereof. The tricyclic dimer will give a polymer with a higher Tg and the linear dimer will have lower Tg. These two products can be useful for creating polymers of dialed thermal characteristics which may be important for processes under which the polymers will be fashioned into components of Navy interests.

-continued

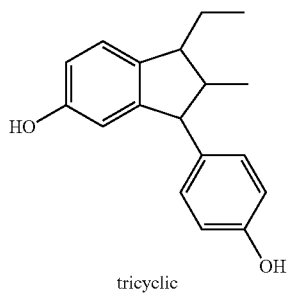

tricyclic

Embodiments of the invention generally relate to processes for making diphenol products including, extracting isomers of 4-methoxyphenylpropene from plant sources, transforming the isomers by olefin cross or self-cross olefin metathesis and at least one catalyst to produce dimeric structures having two equivalents of protected phenolic groups, and deprotecting methyl ethers to yield diphenolic products. Embodiments of the invention further include polymerizing the diphenol products with heat to produce thermoset resins. Other embodiments further include polymerizing the diphenol products with heat to produce thermoplastics. Other embodiments further include polymerizing the diphenol products with

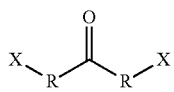

and heat, wherein R includes a benzene ring and X includes a fluorine or chlorine to produce polyetheretherketones.

Yet other embodiments further include polymerizing the diphenol products with

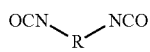

and heat, wherein R comprises a benzene ring to produce polyurethanes. Still yet other embodiments further include polymerizing the diphenol products with

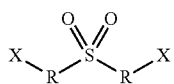

and heat, wherein R includes a benzene ring and X includes a fluorine or chlorine to produce polysulfones. Yet other embodiments further include polymerizing the diphenol products with

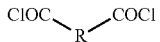

and heat, wherein R includes a benzene ring to produce polyesters. Other embodiments further include polymerizing the diphenol products by reacting two equivalents of 4-fluorophthalic anhydride forming a bis-anhydride, condensation polymerizing the bis-anhydride with an aromatic diamine producing polyetherimides.

In embodiments, the aromatic diamine includes, but is not limited to, 1,3-phenylenediamine. Other embodiments further include polymerizing the diphenol products with

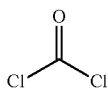

and heat to produce polycarbonates. Yet other embodiments further include polymerizing the diphenol products with BrCN and heat to produce dicyanate esters. Other embodiments further include polymerizing said dicyanate esters with heat to produce cyanurates. While other embodiments further include a catalyst with heat to produce cyanurates.

Other aspects of the invention include the thermoset resins and thermoplastics produced by the processes and methods herein.

Aromatic cyanate ester resins are a unique class of thermosetting polymers that offer a unique combination of low moisture uptake, low dielectric constant, thermochemical stability, and glass transition temperature. Monocyanates (one —OCN group attached to phenyl ring) are not useful for polymerization. Dicyanate esters (two —OCN functional groups attached to phenyl ring(s)) have a majority of polymerizable functional groups: single-ring type (two —OCN groups attached to same phenyl ring)—higher volatility and water uptake limit usefulness as polymerizable species; and "Bisphenol" type (two —OCN groups, each attached to a separate phenyl ring, with a central bridge)—most common type of dicyanate, 2 commercial products, glass transition temperature limited to about 300° C. in practical situations because either 1) the number of —OCN groups per unit volume is lower than needed to achieve glass transition above 300° C., or 2) a more rigid bridge group, which raises glass transition at full cure above 300° C., makes full cure difficult to achieve due to steric hinderance associated with the rigidity of segment between —OCN groups.

Tricyanate esters (& tetracyanate esters, pentacyanate esters, etc.) of more than two —OCN groups attached to phenyl ring, offers a higher density of —OCN groups and therefore are able to achieve glass transition temperatures above 300° C. in practical situation or above 325° C. at full cure. Single ring type (three —OCNs attached to same ring) have high volatility, difficulty controlling reaction, and toxicity concerns limit usefulness for polymerization. Trisphenol type (three —OCNs attached to three separate phenyl rings, also 4-OCN/4-ring, 5-OCN/5-ring, etc.) include 1 commercial product, some other examples in literature, cyanurate density limited to same level as bisphenol type dicyanates, needs flexible bridges between all phenyl rings to achieve complete conversion, glass transition temperature limited to 325° C. at full cure in cases where flexible bridges are used. Mixed ring type (two —OCNs attached to same ring, one —OCN on separate ring. Or, for tetracyanates (two —OCNs each on two phenyl rings) this offers higher cyanurate density than trisphenol type, the key is the number of —OCN groups should exceed the number of phenyl rings.

2 —OCN groups having othro-substitution on the same phenyl ring, results in chemically unstable monomer, not used. 2 —OCN groups having para-substitution on the same phenyl ring, results in steric hindrance and inability to completely polymerize. 3 or more —OCN groups on the same phenyl ring, results in steric hindrance and inability to completely polymerize. 2 or more —OCN groups having meta-substitution on the same phenyl ring—the only type of mixed ring system that can polymerize fully (having fused rings—appear in some patent applications, will not achieve complete cure; having hindered rotation between rings (examples, isopropidyl group, COCl$_2$ group, or more than one bridge attached to an aromatic ring having an attached —OCN group)—appear in some patent applications as co-monomers in multi-component formulations, difficult to achieve cure in a single-component formulation; having free rotation between rings—one example other than invention has dimethylsilyl linkages and a low overall —OCN density, another has fewer rotational degrees of freedom than the embodiments of the invention). Two sub-types are: one-carbon bridges (methylene, ethylidene) not as free to rotate, and two-carbon bridges(ethylene)—more rotational—degrees of freedom. These are all monomers with at least 3 OCN groups attached to phenyl rings, and with the number of —OCN groups exceeding the number of phenyl rings.

JP 01290642 (Hitachi, 1989) describes the formation of cyanate esters for 4 —OCN groups and 2 phenyl rings (both with meta di-substitution), in which there is a single carbon bridge with aliphatic or fluoroaliphatic side groups. Two molecules of this type would have a bridge that allows for free rotation, but based on SciFinder classification, it is not clear if these were actually made. Even these two would have comparatively less rotational freedom than the ethylene bridge found in the resveratrol compound. U.S. Pat. No. 5,260,398 (Liao et al, Dow Chemical) teaches, among many, some cyanate ester monomers having more —OCN groups attached to phenyl rings than phenyl rings, but in which the bridge between phenyl rings contains at least one siloxy group (with at least two attendant carbon atoms). These can be freely rotating or hindered bridges, but the size of the bridge leads to a reduction in the overall number of —OCN groups per unit volume. As a result, the glass transition temperatures of any materials synthesized in the patent do not exceed 290 C. Patent application EP2167478 (WO 2008156443) discloses a tricyanated naphthalene, having 3 —OCN groups on two fused aromatic rings. This fused ring system will not achieve complete cure readily due to steric hindrance (example of 3.3.4.1) The same monomer is included in a list of possible cyanate ester latent hardeners in patent application US 20020058778 and in EP0347800. One other patent application (WO 2000055123) describes unsaturated bridges in cyanate esters containing chlorine or other halogens for flame retardance; these also offer only hindered rotation and will not cure fully.

Embodiments of the invention include structures having: number of —OCNs attached to phenyl rings exceeds number of phenyl rings (provides glass transition temperature of 334° C. when combined with flexible bridge); bridge between rings does not hinder rotation and allows maximum rotational degrees of freedom (allows complete cure at temperatures less than 350° C.); and bridge between rings is small enough to maintain cyanurate density and allows for high char yields.

In embodiments of the invention, the ethylene bridge linking the meta (—OCN di-substituted phenyl ring) to at least one other phenyl —OCN group is the great feature that enables the significant advance in performance.

In embodiments of the invention, two renewable sources of chemical feedstocks were found to contain compounds useful for thermoset compositions which may reduce the dependence on petroleum resources. Applications include aerospace uses requiring high strength-to-weight ratios because the novel materials are lightweight and thermally resistant.

Many composite and polymer materials used in Department of Defense (DoD) applications are derived from crude oil. Foreign supplies of petroleum are the primary source for these chemicals. Efforts that can mitigate or at least decrease DoD dependence on foreign supply of necessary raw materials for essential components will be valuable for long term stability. Embodiments of the invention indicate that biological products from plants can be used to make high-performance materials that could be used for DoD purposes. The products from plants represent renewable chemical feedstocks that can be made into higher value products for the DoD.

In embodiments, plants represent a renewable source of composite materials with only minor chemical modification. Plants have polyphenol compounds called lignans. Plants can be extracted and from these extracts one skilled in the art can isolate particular chemical species. Two examples from the plant kingdom are grapes (*Vitis vinifera*) which grow throughout the world in temperate climates and creosote bush (*Larrea tildentata*) which grows mostly in the arid regions of the southwest USA and northern Mexico. These plants can be extracted and from them isolate resveratrol and dihydroguaiaretic acid (Figure 1). These two polyphenolie compounds can then be chemically transformed by one skilled in the art into corresponding cyanate esters resveratrol tricyanate and dihydroguaiaretic dicyanate. These two plant-derived compounds can them be readily polymerized simply by heating in a controlled fashion. The resulting thermoset resins have high-heat resistance useful for aerospace applications. Thus, plants such as these represent a renewable source of composite materials with only minor chemical modification.

Thermoset resins apply to anything from monomers up through oligomerized and fully converted material, including mixtures and so forth. Resveratrol tricyante, the networks derived from and especially the dihydroresveratrol tricyanate, and the networks derived from it; and even the process for making castings are novel. It was discovered that 0.5 C/min to 240 C works for avoiding an uncontrolled exotherm in this material with an unusually high heat of reaction), regardless of the source. The dihydroresveratrol in particular has a unique combination of structural features (three reactive groups, two phenyl rings, and one ethylene bridge) that impart novel processing, mechanical, and thermal properties, and though we proved it only for the cyanate ester, one could reasonably expect it to be true for other classes of thermosetting monomers (benzoxazines, phthalonitriles, maleimides, nadic and norbornenes, phenyl ethynyl, and possibly azides, with epoxies, acrylics, styrenics, and acetylenes doable but with limited usefulness due to their low thermal stability).

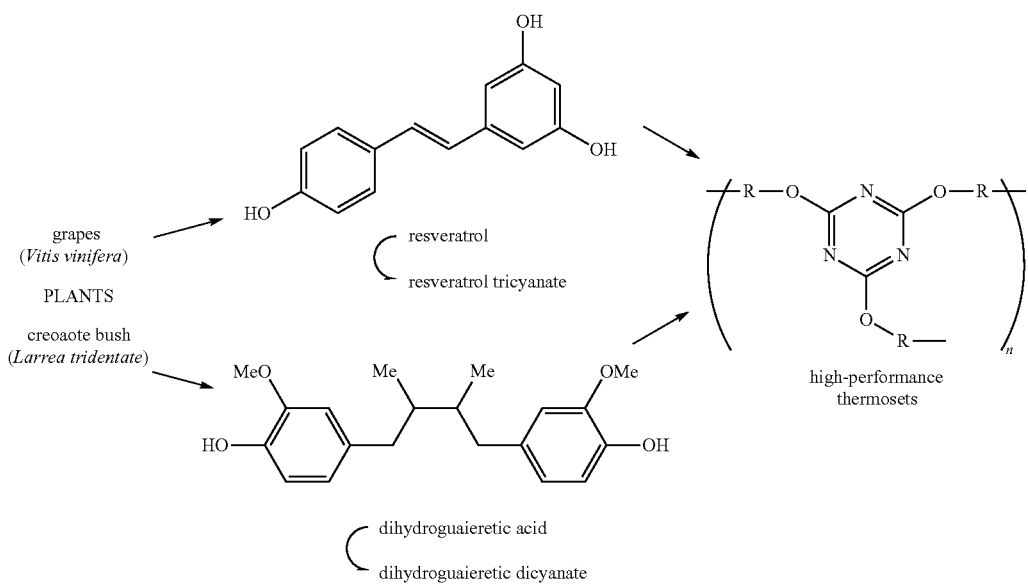

Embodiments of the invention generally relate to processes for making thermoset resins including, extracting polyphenol compounds from at least one plant(s) source having polyphenol compounds, isolating the polyphenols to produce polyphenolic compounds, chemically treating the polyphenolic compounds to produce cyanate esters, and polymerizing the cyanate esters with heat to produce thermoset resins. Other embodiments of the invention generally relate to thermoset resins, resveratrol tricyanates, and dihydroresveratrol tricyanate produced by the process herein.

In embodiments, the polyphenol compounds are, but not limited to, lignans. In embodiments, the plant(s) having polyphenol compounds include, but not limited to, grapes and/or creosote bushes. In other embodiments, the polyphenolic compounds includes resveratrol and/or dihydroguaiaretic acid. In embodiments, the cyanate esters include resveratrol tricyanate and/or dihydroguaiaretic dicyanate. In other embodiments, the thermoset resins includes the general formula 1, wherein "n" ranges from 1 to about 1,000,000,000,000,000,000,000,000,000.

Formula 1

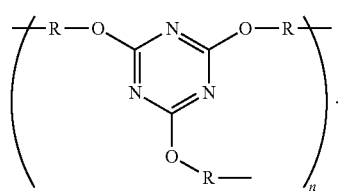

high-performance thermosets

Further embodiments of the invention include the chemical structures below.

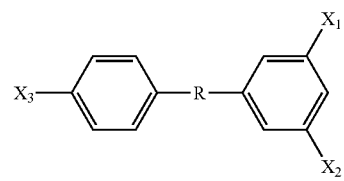

Or

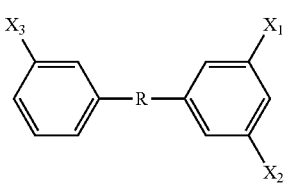

Wherein R=C2Y4, where each Y independently may be —H, —F, —Cl, —Br, or —I; example (C2H2, ethylene), or R=trans-vinylene; and where $X_1$-$X_3$=—OCN (cyanate ester, definitely new), or $X_1$-$X_3$ are each independently selected from glycidyl ether, cyanate ester, or benzoxazine (likely new); note that only R=trans-vinylene may be extracted from a plant, other variants of R require a chemical reaction to transform trans-vinylene to R before transforming —OH to —X.

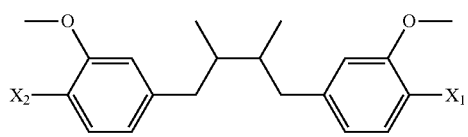

Wherein $X_1$ and $X_2$ are independently selected from glycidyl ether, cyanate ester, or benzoxazine. Note: these are all possible by 1) extraction from a plant 2) chemical treatment (may be multi-step) to yield a reactive monomer, and 3) thermal treatment of reactive monomer with co-reactant (glycidyl ether case only) and/or catalyst (all cases) to yield a macromolecular network polymer. Note that in order to yield the network structure given in claim 6, the reactive monomers must contain at least three fragments of —OCN.

The reactive monomers and the macromolecular networks are also novel even when they are not made by extraction from a plant, but rather by 1) providing resveratrol (or dihydroguaiaretic acid), 2) chemical treatment (may be multi-step) to yield a reactive monomer, and 3) thermal treatment of reactive monomers with co-reactant (glycidyl ether case only) and/or catalyst (all cases) to yield a macromolecular network.

The invention generally relates to renewable feedstocks, and more particularly, to renewable chemical feedstocks derived from the essential oils from herbs and other plants.

In embodiments of the invention, thermosets can be conveniently prepared from the extracts from the essential oils mainly from herbs and other plants. The prepared products can be polymerized or cured into materials with high heat resistance. Decreased reliance on petrochemicals is realized. Applications include aerospace uses requiting high strength-to-weight ratios because the novel materials are lightweight and thermally resistant.

The Navy and Department of Defense (DoD) are heavily dependent on petroleum for sources of mission-critical composite materials. Embodiments of the invention address this issue by employing readily essential oils from plants to make new composite materials. The composite materials may find uses in aerospace applications. The essential oil products from plants represent a renewable resource for resins and plastics.

There are many plants, especially herbs, which provide essential oils when extracted. In particular tarragon (*Artemisia dracunculus*) and star anise (Illicium velum) yield essential oils that are almost exclusively the isomers of 4 methoxyphenylpropene (estragole and anethole). These products transform by the reaction known as olefin metathesis (Figure 1) to give new products that are dimeric in structure having two equivalents of protected phenolic groups in the molecule. The catalyst to carry out this transformation is commercially available to those skilled in the art. The formed point of unsaturation can be reduced or not and then the methyl ethers can be deprotected to yield the new diphenolic products. The diphenolic products from natural and renewable sources can then be inserted into the many known polymerization reactions (Figure 2) to those skilled in the art including, but not limited to, polyesters, polycarbonates, polycyanurates, polyurethanes, polyetherimides, polyetheretherketones, and polysulfones.

In addition, trans-anethole can be dimerized into two different dimers, one di-cyclic and the other tricyclic, by a variety of different acid catalyst (Scheme 1). The resulting diphenols of these dimers possess significantly different properties which will also affect the resulting polymers made thereof. The tricyclic dirtier will give a polymer with a higher Tg and the linear dimer will have lower Tg. These two products can be useful for creating polymers of dialed thermal characteristics which may be important for processes under which the polymers will be fashioned into components of Navy interests.

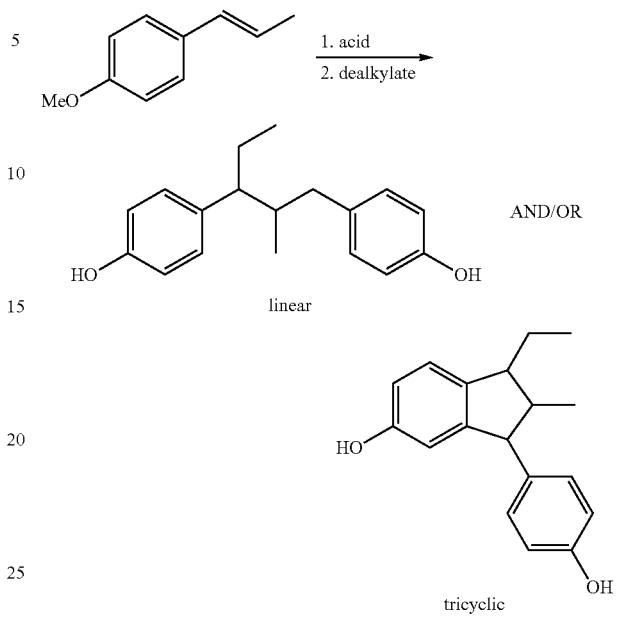

Scheme 1: Dimerization of trans-anethole into linear or tricyclic diphenols.

In one embodiment, trans-anethole is reacted with a ruthenium or similar transition metal catalyst to bring about alkene metathesis. The resulting 4,4'-dimethoxystilbene is then reacted in sequence to give a dicyanate ester: 1. Catalytic hydrogenation; 2. Demethylation with BBr3; 3. Cyanation with BrCN and base

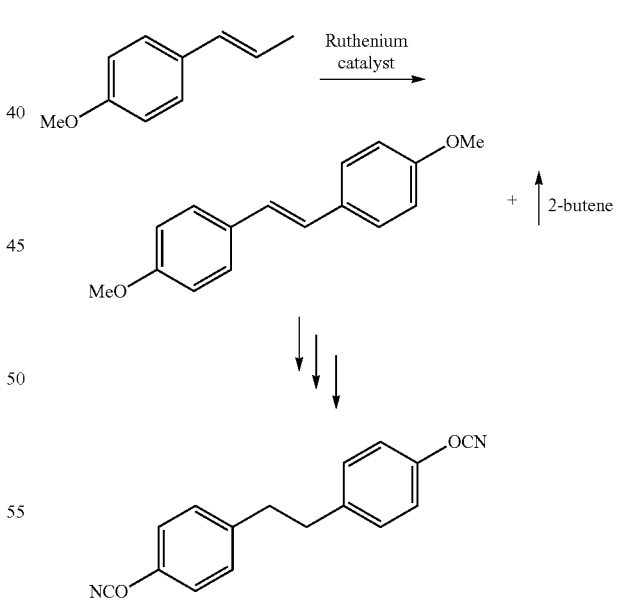

In another embodiment, trans-anethole is exposed to ultraviolet radiation which brings about dimerization. The dimeric cyclobutane product is then reduced by lithium in ammonia to give a diarylbutane derivative (Nozaki et al. *Tetrahedron* 1968, 24, 2183-2192.). Both compounds can then be transformed by the usual reaction sequence to give dicyanate esters.

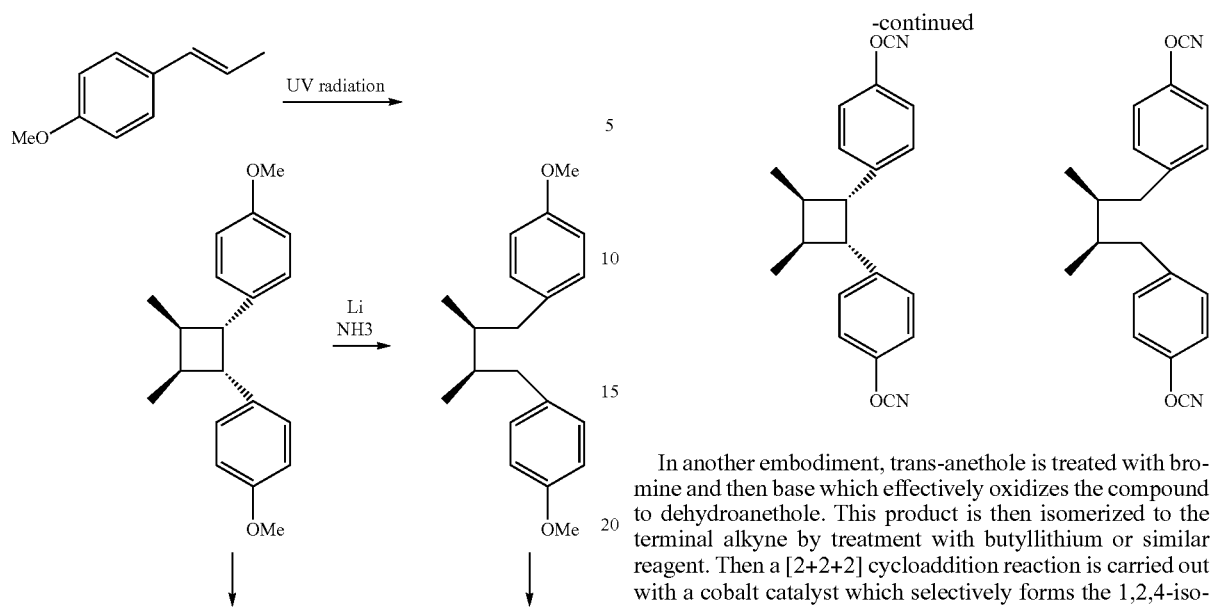

In another embodiment, trans-anethole is treated with bromine and then base which effectively oxidizes the compound to dehydroanethole. This product is then isomerized to the terminal alkyne by treatment with butyllithium or similar reagent. Then a [2+2+2] cycloaddition reaction is carried out with a cobalt catalyst which selectively forms the 1,2,4-isomer rather than the symmetrical isomer. Finally, this 1,2,4-isomer is subjected to the typical sequence to make a tricyanate ester.

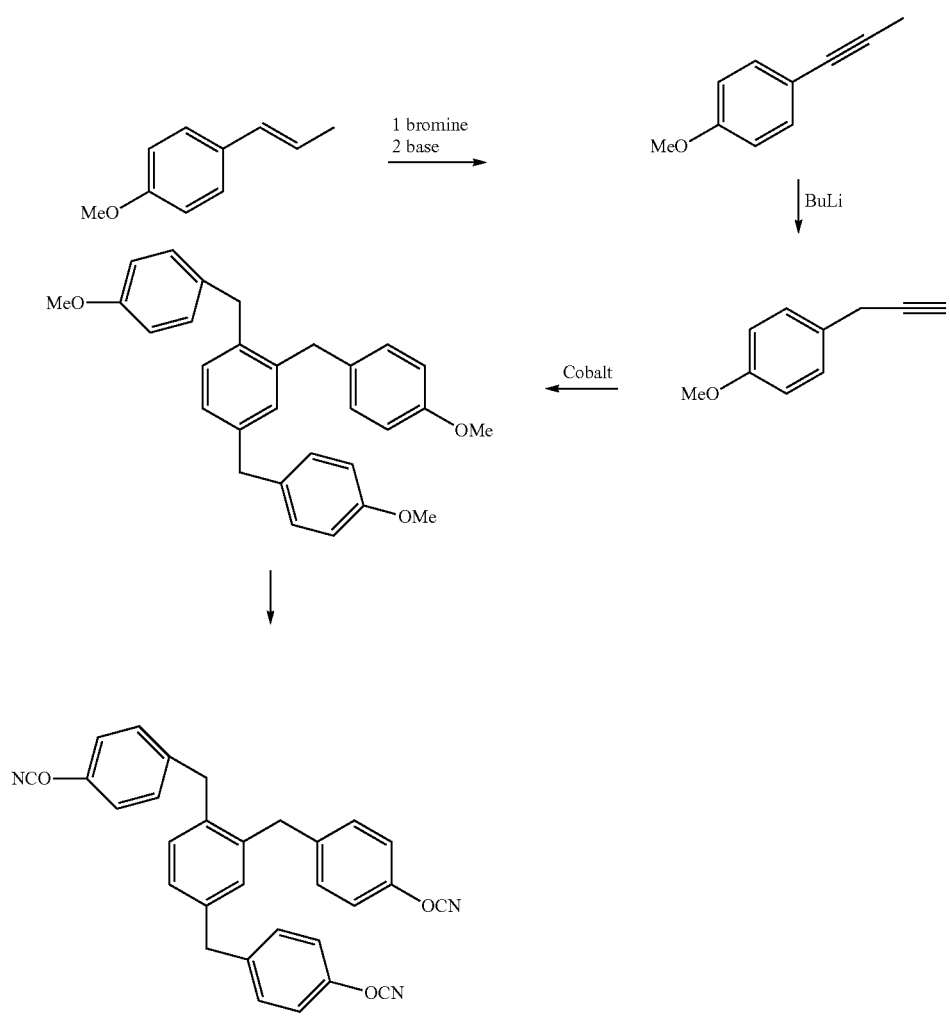

Embodiments of the invention generally relate to methods fir making polymers including, dimerizing trans-anethole by reacting with at least one acid catalyst and dealkylate to produce linear dicyclic diphenols and tricyclic diphenols, polymerizing the linear dicyclic diphenols to produce polymers with lower Tg and/or polymerizing the tricyclic diphenols to produce polymers with higher Tg. Tg is dependent on its use as thermosets and thermoplastics for various platforms. One skilled in the art of the methods described herein and the materials and equivalents utilized herein would be able to determine the lower and higher Tg's of the different embodiments. Another aspect of the invention generally relates to dicyclic and/or tricyclic diphenols produced by the methods herein.

In embodiments, the acid catalyst is selected from the group consisting of sulfuric acid, hydrochloric acid acetic acid, phosphorous acid, and any combination thereof or the like. In other embodiments, the acid catalyst is selected from the group consisting of hydrofluoric acid and other strong acid catalysts. A strong acid is one that ionizes completely in water to form H+ ions and anions. A strong acid is 100% dissociated in solutions of 1.0 M or less. Strong acids protonate the carbonyl, which makes the oxygen positively charged, so that it can easily receive the double bond electrons when the alcohol attacks the carbonyl carbon. In embodiments, the dealkylate is selected from the group consisting of pyridine hydrochloride, boron tribromide, and any combination thereof or the like.

One skilled in the art would appreciate that many acid catalysts, dealkylates can be used and is not limited to the list above, which are examples. In embodiments, the linear dicyclic diphenols includes 1,3-bis(4-hydroxyphenyl)-2-methylpentane. In embodiments, the tricyclic diphenols includes 1-(4-hydroxyphenyl)-2-methyl-3-ethyl-6-hydroxyindane.

Another aspect of the invention generally relates to methods for making dicyanate esters including, dimerizing trans-anethole to produce at least one dicycloaddition, reducing the dicycloaddition with at least one first reducing reagent to produce a diarylbutane derivative(s), demethylation of the diarylbutane(s) to produce dicyanate esters, and/or direct demethylation of the dicycloaddition with at least one second reducing reagent to produce dicyclocyanate esters. Another aspect of the invention generally relates to dicyante esters produced by the methods herein.

In embodiments, the dimerizing the trans-anethole includes exposing the trans-anethole to an effective amount of ultraviolet (UV) radiation to produce at least one dicycloaddition. In embodiments, the dicycloaddition is selected from the group consisting of dimeric cyclobutane(s), 1,2-bis(4-methoxyphenyl)-3,4-dimethylcyclobutane, and any mixtures of dimeric cyclobutane isomers thereof or the like. In embodiments, the first reducing agent(s) is selected from the group consisting of lithium in ammonia, sodium in ammonia, and any combination thereof or the like. In embodiments, the demethylation includes cleaving the methoxy groups and cyanating the diarylbutane derivative(s) with pyridine hydrochloride, boron tribromide, cyanogens bromide, and triethylamide. In embodiments, the diarylbutane derivative(s) includes 1,4-bis(4-methyoxyphenyl)-2,3-dimethylbutane, and mixtures of diarylbutane derivative(s) isomers thereof or the like. In embodiments, the dicyanate esters is selected from the group consisting of 1,4-bis(4-cyanatophenyl)-3,4-dimethylbutane and mixtures of dicyanate ester isomers thereof or the like. One skilled in the art would appreciate that many reagents, cleaving processes, cyanating processes can be used and is not limited to the list above, which are examples.

Embodiments of the invention generally relate to methods for making tricyanate esters including, dimerizing trans-anethole with at least one base and at least one first reagent to produce dehydroanethole having a terminal alkyne, isomerizing the terminal alkyne of the dehydroanethole with isomerizing reagent(s) and carrying out a [2+2+2] cycloaddition reaction with at least one catalyst to selectively form 1,2,4-dehydroanethole isomer(s), and demethylation of the 1,2,4 dehydroanethole isomer(s) with second reagent(s) to form tricyanate esters. Another aspect of the invention generally relates to tricyanate esters produced by the methods herein.

In embodiments, the base is selected from the group consisting of potassium tert-butoxide, potassium hydroxide, sodium amide, and any combination, thereof or the like. In embodiments, the first reagent(s) includes bromine. In embodiments, the dehydroanethole having a terminal alkyne is 1-(4-methoxyphenyl)propyne. In embodiments, the isomerizing reagent(s) includes but are not limited to, butyllithium, tert-butyllithium, and any combination thereof or the like. In embodiments, at least one catalyst is selected from the group consisting of $CoI_2/Zn/ZnBr_2$, organometallic complexes of nickel, palladium, ruthenium, zirconium v combination thereof or the like. In embodiments, the second reagent (s) of the demethylation includes cleaving the methoxy groups and cyanating the diarylbutane derivative(s) with pyridine hydrochloride, boron tribromide, cyanogens bromide, and triethylamide. In embodiments, the tricyanate esters includes 1,2,4-tris(4-cyanatobenzyl)benzene. In embodiments, the 1,2,4 dehydroanethole isomer(s) includes 1,2,4-tris(4-methoxybenzyl)benzene. One skilled in the art would appreciate that many bases, catalysts, isomerizing reagent(s) and reagents, cleaving processes, cyanating processes can be used and is not limited to the list above, which are examples.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fan within the breadth and scope of the claims here appended.

What is claimed is:

1. A method for making polymers, comprising:
   dimerizing trans-anethole by reacting with at least one acid catalyst and dealkylate to produce linear dicyclic diphenols and tricyclic diphenols;
   polymerizing said linear dicyclic diphenols to produce polymers with lower Tg; and/or
   polymerizing said tricyclic diphenols to produce polymers with higher Tg.

2. The methods according to claim 1, wherein said acid catalyst is selected from the group consisting of sulfuric acid, hydrochloric acid acetic acid, phosphorous acid, and any combination thereof or the like.

3. The methods according to claim 1, wherein said acid catalyst is selected from the group consisting of hydrofluoric acid and other strong acid catalysts.

4. The methods according to claim 1, wherein said dealkylate is selected from the group consisting of pyridine hydrochloride, boron tribromide, and any combination thereof or the like.

5. The methods according to claim 1, wherein said linear dicyclic diphenols includes 1,3-bis(4-hydroxyphenyl)-2-methylpentane.

6. The methods according to claim 1, wherein said tricyclic diphenols includes 1-(4-hydroxyphenyl)-2-methyl-3-ethyl-6-hydroxyindane.

7. Dicyclic and/or tricyclic diphenols produced by the methods of claim 1.

8. A method for making dicyanate esters, comprising:
dimerizing trans-anethole to produce at least one dicycloaddition;
reducing said dicycloaddition with at least one first reducing reagent to produce a diarylbutane derivative(s), demethylation of said diarylbutane(s) to produce dicyanate esters; and/or
direct demethylation of said dicycloaddition with at least one second reducing reagent to produce dicyclocyanate esters.

9. The methods according to claim 8, wherein said dimerizing said trans-anethole includes exposing said trans-anethole to an effective amount of ultraviolet (UV) radiation to produce at least one dicycloaddition.

10. The methods according to claim 8, wherein said dicycloaddition is selected from the group consisting of dimeric cyclobutane(s), 1,2-bis(4-methoxyphenyl)-3,4-dimethylcyclobutane, and any mixtures of dimeric cyclobutane isomers thereof or the like.

11. The methods according to claim 8, wherein said first reducing agent(s) is selected from the group consisting of lithium in ammonia, sodium in ammonia, and any combination thereof or the like.

12. The methods according to claim 8, wherein said demethylation comprises cleaving the methoxy groups and cyanating said diarylbutane derivative(s) with pyridine hydrochloride, boron tribromide, cyanogens bromide, and triethylamide.

13. The methods according to claim 8, wherein said diarylbutane derivative(s) includes 1,4-bis(4-methyoxyphenyl)-2,3-dimethylbutane, and mixtures of diarylbutane derivative(s) isomers thereof or the like.

14. The method according to claim 8, wherein said dicyanate este selected from the group consisting of 1,4-bis(4-cyanatophenyl)-3,4-dimethylbutane and mixtures of dicyanate ester isomers thereof or the like.

15. Dicyante esters produced by the methods of claim 8.

16. A method for making tricyanate esters, comprising:
dimerizing trans-anethole with at least one base and at least one first reagent to produce dehydroanethole having a terminal alkyne;
isomerizing said terminal alkyne of said dehydroanethole with isomerizing reagent(s) and carrying out a [2+2+2] cycloaddition reaction with at least one catalyst to selectively form 1,2,4-dehydroanethole isomer(s); and
demethylation of said 1,2,4 dehydroanethole isomer(s) with second reagent(s) to form tricyanate esters.

17. The methods according to claim 16, wherein said base is selected from the group consisting of potassium tert-butoxide, potassium hydroxide, sodium amide, and any combination thereof or the like.

18. The methods according to claim 16, wherein said first reagent(s) includes bromine.

19. The methods according to claim 16, wherein said dehydroanethole having a terminal alkyne is 1-(4-methoxyphenyl)propyne.

20. The methods according to claim 16, wherein said isomerizing reagent(s) butyllithium, tert-butyllithium, and any combination thereof or the like.

21. The methods according to claim 16, wherein at least one said catalyst is selected from the group consisting of CoI2/Zn/ZnBr2, organometallic complexes of nickel, palladium, ruthenium, zirconium, and any combination thereof or the like.

22. The methods according to claim 16, wherein said second reagent(s) of said demethylation comprises cleaving the methoxy groups and cyanating said diarylbutane derivative(s) with pyridine hydrochloride, boron tribromide, cyanogens bromide, and triethylamide.

23. The methods according to claim 16, wherein said tricycanate esters includes 1,2,4-tris(4-cyanatobenzyl)benzene.

24. The methods according to claim 16, wherein said 1,2,4 dehydroanethole isomer(s) includes 1,2,4-tris(4-methoxybenzyl)benzene.

25. Tricyanate esters produced by the methods of claim 16.

* * * * *